US00PP21118P2

(12) United States Plant Patent
Brown

(10) Patent No.: US PP21,118 P2
(45) Date of Patent: Jun. 29, 2010

(54) ***PETUNIA* PLANT NAMED 'MP3'**

(50) Latin Name: *Petunia×hybrida*
Varietal Denomination: MP3

(75) Inventor: Graham Noel Brown, Pennant Hills (AU)

(73) Assignee: NuFlora International Pty. Ltd., Glenfield, NSW (AU)

( * ) Notice: Subject to any disclaimer, the term of this patent is extended or adjusted under 35 U.S.C. 154(b) by 2174 days.

(21) Appl. No.: 10/259,964

(22) Filed: Sep. 29, 2002

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP12,857 P2 * 8/2002 Brown ..... Plt./356

OTHER PUBLICATIONS

UPOV-ROM GTITM Computer Database, GTI Jouve Retrieval Software, citation(s) for 'MP3'.*
http://www.hardyboyplant.com/newpots2.html.*

* cited by examiner

*Primary Examiner*—Bruce R Campell
*Assistant Examiner*—W. C. Haas
(74) *Attorney, Agent, or Firm*—C. A. Whealy

(57) ABSTRACT

A new and distinct cultivar of *Petunia* plant named 'MP3', characterized by its compact and outwardly spreading plant habit; freely and continuous branching habit; small leaf size; numerous small dark violet-colored flowers; and resistance to Botrytis and Powdery Mildew.

1 Drawing Sheet

Botanical classification: *Petunia×hybrida* cultivar MP3.

BACKGROUND OF THE INVENTION

The present Invention relates to a new and distinct cultivar of *Petunia* plant, botanically known as *Petunia×hybrida*, and hereinafter referred to by the cultivar name MP3.

The new *Petunia* is a product of a planned breeding program conducted by the Inventor in Cobbitty, New South Wales, Australia. The objective of the breeding program is to create outwardly spreading *Petunias* with numerous small flowers with attractive flower colors.

The new *Petunia* originated from a cross-pollination made by the Inventor in 1999 of a proprietary *Petunia* selection identified as X98.31, not patented, as the female, or seed parent, with a proprietary *Petunia* selection identified as X97.66, not patented, as the male, or pollen parent. The new *Petunia* was selected as a single plant from the resulting progeny of the cross-pollination by the Inventor in 1999, in Cobbitty, New South Wales, Australia, on the basis of its outwardly spreading habit and numerous small flowers.

Asexual reproduction of the new cultivar by vegetative cuttings taken in Cobbitty, New South Wales, Australia since 1999 has shown that the unique features of this new *Petunia* are stable and reproduced true to type in successive generations.

SUMMARY OF THE INVENTION

Plants of the cultivar MP3 have not been observed under all possible environmental conditions. The phenotype may vary somewhat with variations in environment such as temperature and light intensity without, however, any variance in genotype.

The following traits have been repeatedly observed and are determined to be the unique characteristics of 'MP3'. These characteristics in combination distinguish 'MP3' as a new and distinct cultivar:

1. Compact and outwardly spreading plant habit.
2. Freely branching habit.
3. Small leaf size.
4. Numerous small dark violet-colored flowers.
5. Resistant to Botrytis and Powdery Mildew.

Compared to plants of the female parent, plants of the new *Petunia* have smaller flowers, flower earlier and differ in flower color. Compared to plants of the male parent, plants of the new *Petunia* have smaller flowers and flower earlier.

Plants of the new *Petunia* can be compared to plants of the cultivar MP20, disclosed in U.S. Plant Pat. No. 12,857. In side-by-side comparisons conducted in Cobbitty, New South Wales, Australia, plants of the new *Petunia* differed from plants of the cultivar MP20 in the following characteristics:

1. Plants of the new *Petunia* had smaller flowers than plants of the cultivar MP20.
2. Flowers of plants of the new *Petunia* had less prominent venation than flowers of plants of the cultivar MP20.
3. Plants of the new *Petunia* and the cultivar MP20 differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

Colors in the photographs may differ slightly from the color values cited in the detailed botanical description which accurately describe the colors of the new *Petunia*.

The photograph at the top of the sheet comprises a side perspective view of a typical flowering plant of 'MP3' grown in a container.

The photograph at the bottom of the sheet comprises a close-up view of typical flower buds, flowers and the upper and lower surfaces of typical leaves of 'MP3'.

DETAILED BOTANICAL DESCRIPTION

The aforementioned photographs and following observations and measurements describe plants grown in Lompoc, Calif., under commercial practice during the winter and spring in a polycarbonate-covered greenhouse with day temperatures about 18 to 24° C., night temperatures about 16 to 18° C. and light levels about 5,000 to 9,000 foot-candles. Plants were grown with one rooted cutting per 15.25-cm container for about 12 weeks. In the following description, color references are made to The Royal Horticultural Society Colour Chart, 1995 Edition, except where general terms of ordinary dictionary significance are used.

Botanical classification: *Petunia×hybrida* cultivar MP3.

Parentage:

*Female parent.*—Proprietary *Petunia* selection identified as X98.31, not patented.

*Male parent.*—Proprietary *Petunia* selection identified as X97.66, not patented.

Propagation:

*Type cutting.*—Vegetative cuttings.

*Time to initiate roots.*—About 14 days at 22° C.

*Time to develop roots.*—About 28 days at 22° C.

*Root description.*—Fine, fibrous, whitish in color.

*Rooting habit.*—Freely branching, dense.

Plant description:

*Form.*—Annual flowering plant; indeterminate; compact; initially upright, then outwardly spreading to low trailing; plants eventually becoming hemispherical in shape. Moderately vigorous. Freely basal branching with about ten main lateral branches per plant with lateral branches potentially forming at every node.

*Usage.*—Appropriate for hanging baskets, window boxes, patio containers and landscape applications.

*Plant height.*—About 10 cm.

*Plant diameter.*—About 40 cm.

*Lateral branches.*—Length: About 20 cm. Diameter: About 2 mm. Internode length: About 1.5 cm. Texture: Pubescent. Color: 144A.

*Foliage description.*—Arrangement, before flowering: Alternate, simple. Arrangement, when flowering: Opposite, simple. Length: About 2.4 cm. Width: About 1.2 cm. Shape: Elliptical. Apex: Acute. Base: Attenuate. Margin: Entire. Texture: Glandular, viscid; upper surface, glabrous; lower surface, slightly pubescent. Venation pattern: Pinnate. Color: Young and fully expanded foliage, upper surface: 146A. Young and fully expanded foliage, lower surface: 146B. Venation, upper and lower surfaces: 146B. Petiole length: About 6 mm. Petiole diameter: About 1 mm. Petiole color: 144B.

Flower description:

*Flower type and habit.*—Small salverform flowers; flowers face mostly upward or outward; single, axillary. Flowers persistent. Freely flowering, typically about 400 open flowers and flower buds per plant.

*Natural flowering season.*—Long day responsive; spring until frost in the autumn; flowering continuous during the flowering period.

*Flower longevity on the plant.*—About 7 days.

*Fragrance.*—Not detected.

*Flower size.*—Diameter: About 2.8 cm. Tube length: About 2.7 cm. Throat diameter, distal end: About 7 mm. Tube diameter, proximal end: About 2.5 mm.

*Flower buds.*—Length: About 1.3 cm. Diameter: Apex: About 3 mm. Base: About 2 mm. Shape: Elongated oblong with ruffled apices Color: 79D.

*Corolla.*—Arrangement/appearance: Single whorl of five petals, fused into flared trumpet with distinct clefts between petal lobes. Petal length from throat: About 1.4 cm. Petal width: About 1.2 cm. Petal shape: Roughly spatulate or fan-shaped. Petal apex: Rounded, cuspidate; slightly ruffled. Petal margin: Entire; slightly ruffled. Petal texture: Smooth, velvety. Color: Petal, upper surface, when opening: 83A. Petal, lower surface, when opening: 79C. Petal, upper surface, fully opened: 83A with irregular patches of 83B; color does not fade with subsequent development. Petal, lower surface, fully opened: 79C with irregular patches of 79D. Flower throat (inside): Darker than 79A. Flower tube (outside): 79A. Venation, upper petal surface: 83A. Venation, lower petal surface: 79B. Venation, throat: Darker than 79A. Venation, tube: 79A.

*Sepals.*—Arrangement/appearance: Single whorl of five sepals fused at base, star-shaped. Length: About 1 cm. Width: About 2 mm. Shape: Ligulate. Apex: Rounded. Margin: Entire. Texture, both surfaces: Glandular, coarse. Color, upper and lower surfaces: 138A.

*Peduncles.*—Length: About 2.25 cm. Width: About 1.25 mm. Angle: About 45 to 90° to the stem. Strength: Moderately strong; wiry. Texture: Pubescent. Color: 144A.

*Reproductive organs.*—Stamens: Quantity/arrangement: Five, adnate to corolla tube. Anther shape: Ovoid. Anther length: About 1.5 mm. Anther color: 84A. Pollen amount: Scarce to moderate. Pollen color: 97B. Pistils: Quantity: One. Pistil length: About 1.8 cm. Stigma shape: Anvil-shaped. Stigma color: 144B. Style length: About 1.4 cm. Style color: 79C. Ovary color: 145A.

*Fruit/seed.*—Fruit and seed production has not been observed.

Disease/pest resistance: Plants of the new *Petunia* have been observed to have good resistance to Botrytis and Powdery Mildew. Plants of the new *Petunia* have not been noted to be resistant to pests common to *Petunia*.

It is claimed:

1. A new and distinct cultivar of *Petunia* plant named 'MP3', as illustrated and described.

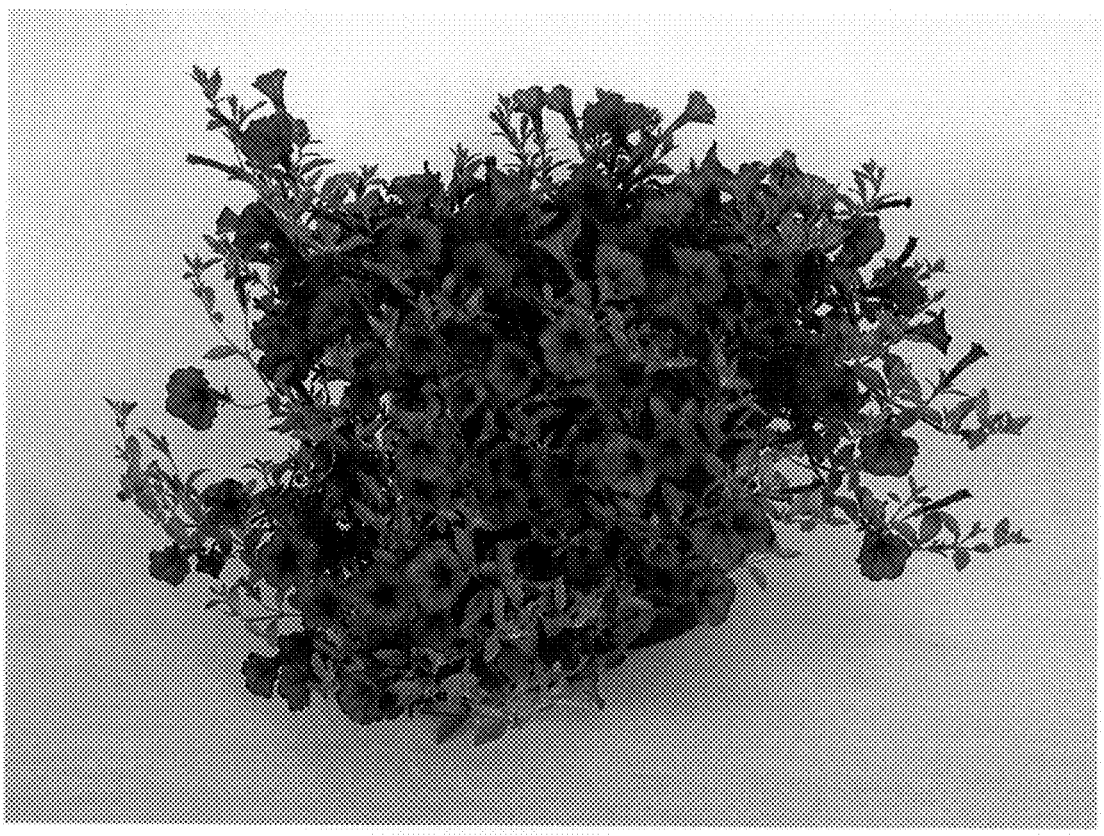
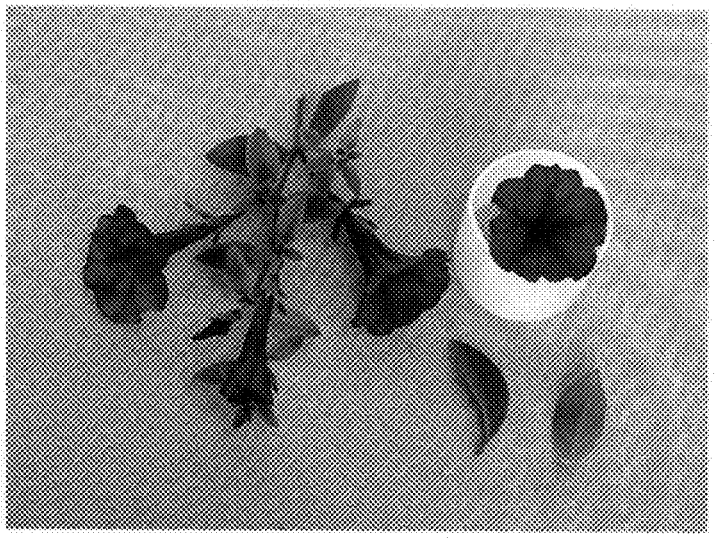

* * * * *